(12) United States Patent  
Anderson et al.

(10) Patent No.: US 8,992,492 B2  
(45) Date of Patent: Mar. 31, 2015

(54) NEGATIVE PRESSURE WOUND TREATMENT DEVICE, AND METHODS

(75) Inventors: Paul J. Anderson, Eden Prairie, MN (US); Douglas Duchon, Chanhassen, MN (US)

(73) Assignee: Wound Care Technologies, Inc., Chanhassen, MN (US)

( * ) Notice: Subject to any disclaimer, the term of this patent is extended or adjusted under 35 U.S.C. 154(b) by 518 days.

(21) Appl. No.: 13/246,369

(22) Filed: Sep. 27, 2011

(65) Prior Publication Data

US 2012/0095420 A1  Apr. 19, 2012

Related U.S. Application Data

(63) Continuation of application No. 11/818,059, filed on Jun. 12, 2007, now Pat. No. 8,025,650.

(60) Provisional application No. 60/804,513, filed on Jun. 12, 2006.

(51) Int. Cl.  
*A61M 1/00* (2006.01)

(52) U.S. Cl.  
CPC ............ *A61M 1/0023* (2013.01); *A61M 1/0088* (2013.01); *A61M 2209/088* (2013.01)  
USPC ........................................................ 604/313

(58) Field of Classification Search  
USPC .................... 604/304, 305, 307, 313; 602/46  
See application file for complete search history.

(56) References Cited

U.S. PATENT DOCUMENTS

| | | |
|---|---|---|
| 3,783,870 A | 1/1974 | Schachet |
| 3,809,086 A | 5/1974 | Schachet et al. |
| 3,809,087 A | 5/1974 | Lewis, Jr. |
| 4,073,294 A | 2/1978 | Stanley et al. |
| 4,266,545 A | 5/1981 | Moss |
| 4,278,089 A | 7/1981 | Huck et al. |
| 4,392,860 A | 7/1983 | Huck et al. |
| 4,569,674 A | 2/1986 | Phillips et al. |
| 4,578,060 A | 3/1986 | Huck et al. |
| 4,655,754 A | 4/1987 | Richmond et al. |
| 4,661,093 A | 4/1987 | Beck et al. |
| 4,713,052 A | 12/1987 | Beck et al. |
| 4,798,583 A | 1/1989 | Beck et al. |
| 4,826,494 A | 5/1989 | Richmond et al. |
| 4,923,444 A | 5/1990 | Daoud et al. |
| 4,936,834 A | 6/1990 | Beck et al. |
| 4,969,880 A | 11/1990 | Zamierowski |
| 5,100,395 A | 3/1992 | Rosenberg |
| 5,141,503 A | 8/1992 | Sewell, Jr. |
| 5,549,584 A | 8/1996 | Gross |

(Continued)

FOREIGN PATENT DOCUMENTS

GB    2 307 180 A    5/1997

OTHER PUBLICATIONS

US 6,216,701, 04/2001, Heaton et al. (withdrawn).

(Continued)

*Primary Examiner* — Melanie Hand  
(74) *Attorney, Agent, or Firm* — Merchant & Gould P.C.

(57) ABSTRACT

A negative pressure (i.e., vacuum or suction) wound healing device and system incorporating the device. The device of the present disclosure is smaller, lighter, portable, and overall more manageable by both the user and the medical personnel than the conventional systems. The device could be readily worn by the user.

13 Claims, 5 Drawing Sheets

(56) References Cited

U.S. PATENT DOCUMENTS

| | | | |
|---|---|---|---|
| 5,636,643 A | 6/1997 | Argenta et al. |
| 5,645,081 A | 7/1997 | Argenta et al. |
| D406,899 S | 3/1999 | Cottle |
| 5,944,703 A | 8/1999 | Dixon et al. |
| 6,024,731 A | 2/2000 | Seddon et al. |
| 6,135,116 A | 10/2000 | Vogel et al. |
| D434,150 S | 11/2000 | Tumey et al. |
| 6,142,982 A | 11/2000 | Hunt et al. |
| D439,341 S | 3/2001 | Tumey et al. |
| 6,261,276 B1 | 7/2001 | Reitsma |
| 6,345,623 B1 | 2/2002 | Heaton et al. |
| 6,458,109 B1 | 10/2002 | Henley et al. |
| 6,553,998 B2 | 4/2003 | Heaton et al. |
| 6,648,862 B2 | 11/2003 | Watson |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 8,025,650 B2 | 9/2011 | Anderson et al. |
| 2002/0143286 A1 | 10/2002 | Tumey |
| 2002/0183702 A1 | 12/2002 | Henley et al. |
| 2003/0093041 A1 | 5/2003 | Risk, Jr. et al. |
| 2003/0212357 A1 | 11/2003 | Pace |
| 2004/0073151 A1 | 4/2004 | Weston |
| 2004/0121438 A1 | 6/2004 | Quirk |
| 2004/0243073 A1 | 12/2004 | Lockwood et al. |
| 2005/0010153 A1 | 1/2005 | Lockwood et al. |
| 2005/0020955 A1 | 1/2005 | Sanders et al. |
| 2005/0070858 A1 | 3/2005 | Lockwood et al. |
| 2005/0085795 A1 | 4/2005 | Lockwood et al. |
| 2005/0148913 A1 | 7/2005 | Weston |
| 2005/0203452 A1 | 9/2005 | Weston et al. |
| 2005/0222527 A1 | 10/2005 | Miller et al. |
| 2005/0222528 A1 | 10/2005 | Weston |
| 2005/0261642 A1 | 11/2005 | Weston |
| 2006/0015087 A1 | 1/2006 | Risk, Jr. et al. |
| 2006/0100586 A1 | 5/2006 | Karpowicz et al. |
| 2006/0173253 A1 | 8/2006 | Ganapathy et al. |

OTHER PUBLICATIONS

Blue Sky Medical, 1 page (Publicly known at least as early as Jun. 12, 2007).

The V.A.C.® ATS® System, *KCI Licensing, Inc.*, 3 pages. (Publicly known at least as early as Jun. 12, 2007).

The V.A.C.® Freedom® System, *KCI Licensing, Inc.*, 3 pages (Publicly known at least as early as Jun. 12, 2007).

V.A.C.® Canisters, *KCI Licensing, Inc.*, 4 pages (Copyright 1998-2006).

"KCI Introduces New Vacuum Assisted Closure™ Product; V.A.C.® Freedom™ Device Continues Company's Leadership in Advanced Wound Healing Systems," *PR Newswire* (Oct. 2002).

V.A.C. ® Freedom™ System Product information, www.kci1.com.

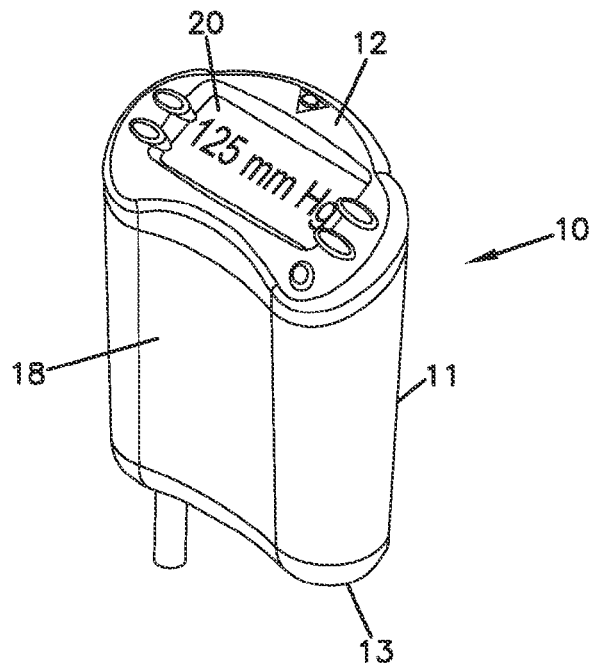
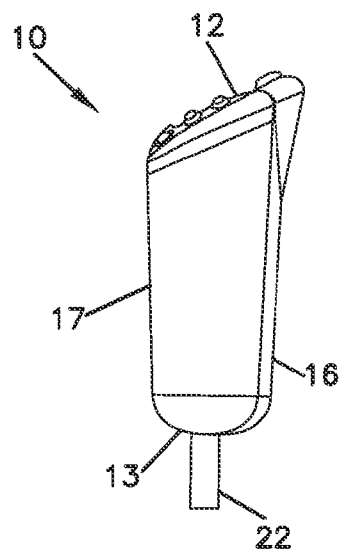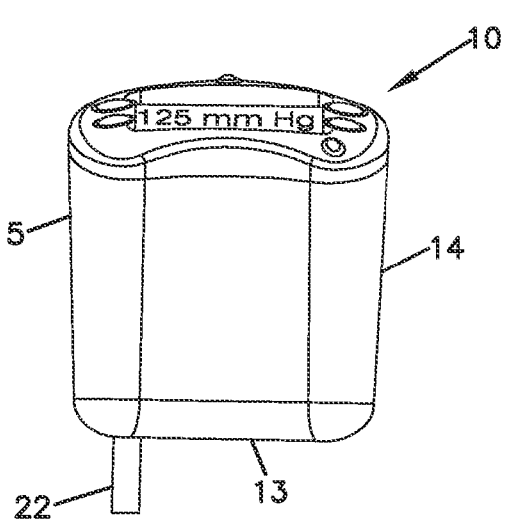

NEGATIVE PRESSURE WOUND TREATMENT DEVICE, AND METHODS

CROSS REFERENCE TO RELATED APPLICATIONS

This application is a continuation of application Ser. No. 11/818,059, filed Jun. 12, 2007, now U.S. Patent No. 8,025,650, which claims the benefit of provisional application Ser. No. 60/804,513, filed Jun. 12, 2006, which applications are incorporated herein by reference in their entirety.

TECHNICAL FIELD

The present disclosure generally relates to rigid, yet disposable, plastic containers, particularly resealable and reusable plastic containers, and methods of using.

BACKGROUND

Around the 1950's, Russian researchers began experimenting with pulling a vacuum on open flesh wounds in an attempt to speed healing of the wounds. A vacuum was placed at or close to the surface of the wound and exudate was suctioned and removed from the wound. Although this technology has progressed over the years, there are currently only a few commercially active companies with vacuum or negative pressure devices for open wounds.

Kinetic Concepts Inc. (aka, KCI) is one such company. KCI has two products on the market, the V.A.C.® Freedom® System and the V.A.C.® ATS® System.

KCI advertises the V.A.C.® Freedom® System as a portable system for advanced wound healing. The V.A.C.® Freedom® System is advertised as a lightweight and portable system, designed to help patients return to work and daily activities. It features patented technology for safe, controlled wound healing. It has an adjustable rate of dressing-drawdown intensity for increased patient comfort, and potentially reduces the number of dressing changes and nursing visits over traditional wound care. The system includes a large 300 ml canister to minimize canister changes, and the canister is said to be easily removed and replaced. A filter system is present to minimize wound odor. The system is advertised as having long battery life (e.g., up to 12 hours), which enables patients to be mobile for a full day. The On-Screen User Guide of the system saves time, the T.R.A.C.® Pad® of the system simplifies dressing changes, and Smart Alarms™ (e.g., including audible and visible alarms) of the system help ensure patient safety. This system is, according to KCI, a lightweight and portable system that helps patients return to work and daily activities. A carrying case allows discreet delivery of therapy. The V.A.C.® Freedom® unit is 6.5" (16.5 cm) wide by 3.125" (7.9 cm) high by 7.5" (19.1 cm) deep. It weighs 3.20 lbs. (1.45 kg).

KCI also has the V.A.C.® ATS® System, which is advertised as being designed for higher acuity wounds for patients in acute care and long-term care facilities. The V.A.C.® ATS® System features patented Therapeutic Regulated Accurate Care (T.R.A.C.®) technology for safe, controlled wound healing. This system includes audible and visual alarms, and has a battery life of approximately 4 hours. Canister volumes of 500 and 1,000 mL are available. The V.A.C.® ATS® unit is 14.6" (37 cm) wide by 11" (28 cm) high by 7.1" (18 cm) deep. It weighs 12.3 lbs. (5.6 kg).

KCI also provides replacement canisters for both of the V.A.C.® systems.

Blue Sky Medical is another company that is active in vacuum or negative pressure devices for open wounds. Blue Sky Medical markets the Versatile 1™ wound vacuum system. This system includes the Versatile 1™ Pump with a 15 foot power cord, a small 250 mL autoclavable canister, a large (800 cc) disposable canister (which uses a hoop adaptor), and a pump-canister connector. This system includes bacteria/overflow filters.

Although these products have serviced the wound healing industry well, alternate options are desirable.

SUMMARY OF THE DISCLOSURE

The present disclosure is directed to a negative pressure (i.e., vacuum) wound healing device.

The demand for negative pressure wound healing devices is large and growing fast. Conventional negative pressure wound healing devices and systems, such as those discussed above, are large, expensive, and not very portable. The process of applying the custom dressing is tedious and time consuming. There is frequently pain and discomfort associated with higher levels of vacuum pressure that are applied to wounds. There is a need for a much smaller, lighter, more portable, less expensive, less painful, easier to use negative pressure wound healing device. The present disclosure describes a device, with numerous optional features, that provides improved wound healing.

The device of the present disclosure is smaller, lighter, more portable, and overall more manageable by both the user and the medical personnel than the conventional systems. The device can be readily worn by the user.

These and various other features which characterize the device and system of this disclosure are pointed out with particularity in the attached claims. For a better understanding of the systems and the devices of the disclosure, their advantages, their use and objectives obtained by their use, reference should be made to the drawings and to the accompanying description, in which there is illustrated and described preferred embodiments of this disclosure.

BRIEF DESCRIPTION OF THE DRAWINGS

FIG. 4 is a perspective view of a device having features that are examples of inventive aspects in accordance with the principles of the present disclosure, showing the front, top and right side of the device;

FIG. 5 is a right side view of the device of FIG. 4, the left side view being similar;

FIG. 6 is a front view of the device of FIG. 4;

DETAILED DESCRIPTION OF A PREFERRED EMBODIMENT

Figure 1:
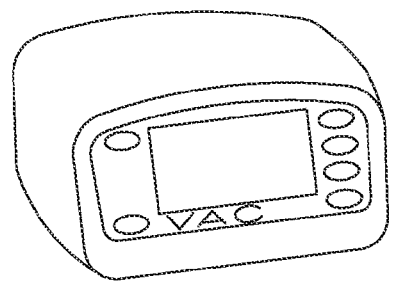
FIG. 1 illustrates the prior art V.A.C.® Freedom® System.
Figure 2:
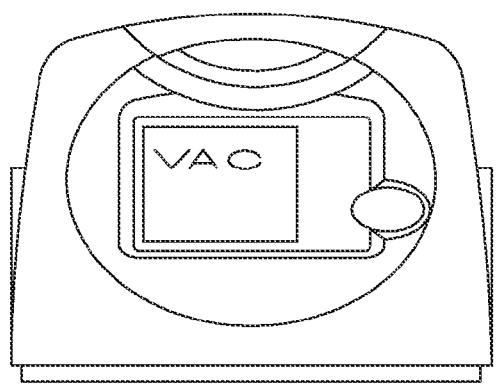
FIG. 2 illustrates the prior art V.A.C.® ATS® System.
Figure 3:
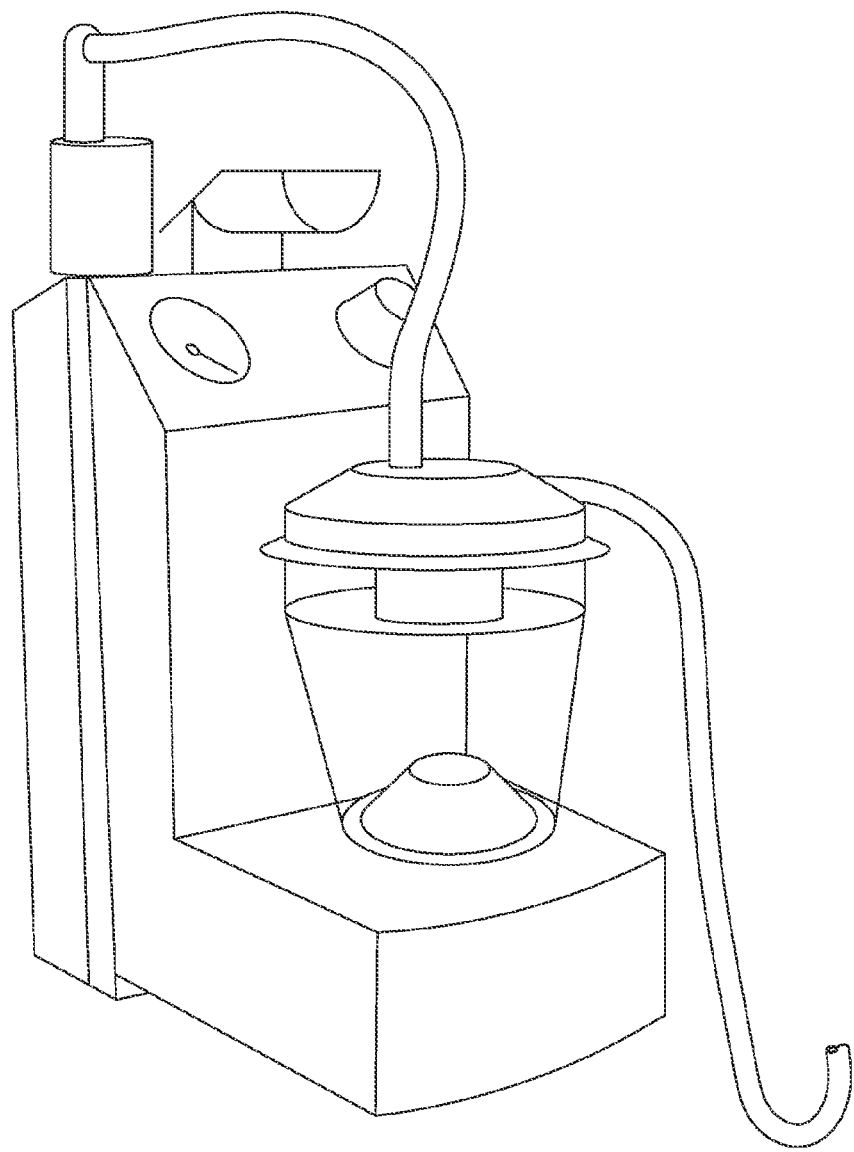
FIG. 3 illustrates the prior art Versatile 1™ wound vacuum system.
Figure 7:
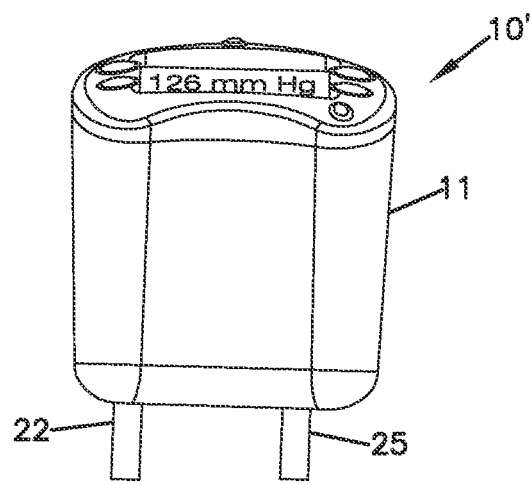
FIG. 7 is a front view of a second embodiment of a device having features that are examples of inventive aspects in accordance with the principles of the present disclosure.

The present disclosure is directed to a negative pressure wound therapy device, which is applied to a wound in order to stimulate healing. By applying controlled negative pressure (i.e., vacuum or suction) to a wound, excessive fluids are removed, cells are stimulated to proliferate, angiogenesis is accelerated, and the sustained contraction helps to draw the wound closed. Negative pressure wound therapy can be effective in both chronic and acute wounds.

Negative pressure wound therapy often utilizes a reticulated sponge, a form that distributes pressure evenly throughout the sponge regardless of where the negative pressure is applied. The sponge may be cut to fit the size and depth of the wound. After the wound is filled with a sponge, the area may be covered with a semi occlusive clear drape and connected via a tube to a canister that is attached to a computer-controlled unit that applies the programmed suction. The negative pressure system gently pulls out stagnant fluids, such as wound drainage or stagnant fluid surrounding the wound. This exudate is removed from the wound and collected, such as in a sealed canister.

There are a number of major benefits of using negative pressure wound therapy in stimulating wound healing. A number of the major benefits of this type of therapy are discussed briefly, as follows:

1. Protection: By placing a semi-occlusive drape over the open wound, a closed wound environment is created. This is beneficial in that it protects the wound from external contaminants. This also helps protect other patients and healthcare staff from potential cross contamination. Dressing changes are normally performed every 48 hours with negative pressure wound therapy.

2. Blood flow: Negative pressure wound therapy supports blood flow to and from the wound bed. Adequate blood flow supports a moist wound environment. Without negative pressure therapy, the wounds may develop a zone of stasis or stagnant wound fluid, around the wound. This stagnant fluid can prevent blood from reaching the defect. By applying controlled negative pressure that helps to alleviate this redundant fluid, blood can flow into the wound bed. Negative pressure, when applied at appropriate levels, can also enhance angiogenesis, the development of new capillaries, that supply the wound bed with the healing properties that only blood can provide, such as oxygen, white blood cells, and nutrients. Negative pressure wound therapy does not normally re-vascularize a patient. It does, however, assist circulation to the wound bed by removing obstacles such as stagnant fluid.

3. Decreased bacterial load: By removing stagnant wound fluid, which is a fantastic medium for organisms, the bacterial load may be reduced. In addition, negative pressure wound therapy may also enhance infection control by supporting blood flow, which is a vital aspect for fighting infection.

4. Increased proliferation: Controlled negative pressure may help the wound get smaller at a faster rate than without negative pressure. As the foam dressing contracts, the tissue cells are stretched, which may encourage the cells to multiply. Research has proven that mechanically stretching cells encourages them to proliferate at an increased rate. A cell normally desires to have a round shape and be buoyant. If stretched and irritated, the cell divides so it can resume its normal shape. Continued irritation, via the negative pressure, can increase the rate of tissue re-growth dramatically.

5. Wound contraction: The mechanisms in place during negative pressure wound therapy speed the rate of wound contraction. When negative pressure is applied to the wound, the wound contracts. This contraction is supported during the therapy, much like a brace or splint. As the dynamics within the wound enhance healing, contraction is also accelerated.

Referring now to the figures of the present disclosure, a vacuum pressure device having features that are examples of inventive aspects in accordance with the principles of the present disclosure is illustrated in FIGS. 4 through 7.

Referring to FIGS. 4 through 6, one embodiment of a negative pressure wound healing device 10 is illustrated. Device 10 includes a housing 11 having a top surface 12, a bottom surface 13, a first (e.g., right) side 14, a second or opposite (e.g., left) side 15, a back side 16 and a front side 17. In the illustrated embodiment, front side 17 includes a concave portion 18.

The top surface 12 may include instrumentation 20, which can include a display screen, knobs, actuator buttons, on/off switch, etc. Although depicted as being included on the top surface 12, it should be noted that the instrumentation 20 may be included on other sides of the device 10.

Device 10 is configured to provide a negative pressure, vacuum, suction, or other decreased pressure to a wound. Extending from bottom surface 13 is an input line 22, for operable connection of device 10 to the wound. The negative pressure is applied to the wound via line 22.

Device 10 is a portable, small, lightweight device that facilitates carrying or otherwise moving around. By reducing the size and/or power consumption of the various elements of device 10 (e.g., reducing the size and energy consumption of a pump of the device, reducing the size of a battery of the device, etc.) a small, portable negative pressure wound healing device is provided that is much more convenient for the patient and caregiver.

In certain embodiments, device 10 weighs no more than about 3 lbs, often no more than about 2.5 lbs. In other embodiments, device 10 weighs no more than about 2 lbs or even no more than about 1.5 lbs. Device 10, particularly housing 11, may have a volume of no more than about 150 in$^3$, often no more than about 125 in$^3$. Various examples of dimensions for device 10 include, 5 in wide by 5 in high by 2 in deep (50 in$^3$), 6 in wide by 7 in high by 3 in deep (126 in$^3$), 4 in wide by 8 in high by 3 in deep (96 in$^3$), and 8 in wide by 5 in high by 3 inch deep (120 in$^3$). It should be understood that generally any combination of these dimensions and ranges within these dimensions could be used for device 10. In certain embodiments, device 10 may be shaped and sized to be easily held in the palm of the user's hand.

The device 10 is designed to utilize space within housing 11, resulting in the small volume of the device 10. For example, in certain embodiments, the device 10 may have a high capacity battery, which might be rechargeable while within housing 11 or after being removed therefrom. The battery may be designed for, for example, 12 hours, 24 hours or more of operation, depending on the run time desired.

Figure 9:
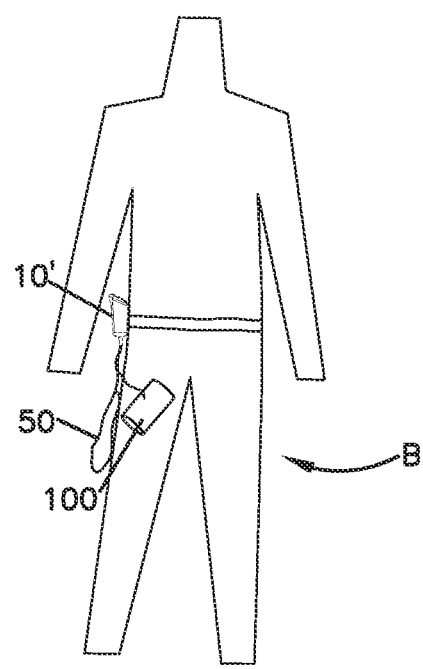
FIG. 9 is a schematic diagram illustrating a user having the device of FIG. 7 affixed to his/her body.
Figure 8:
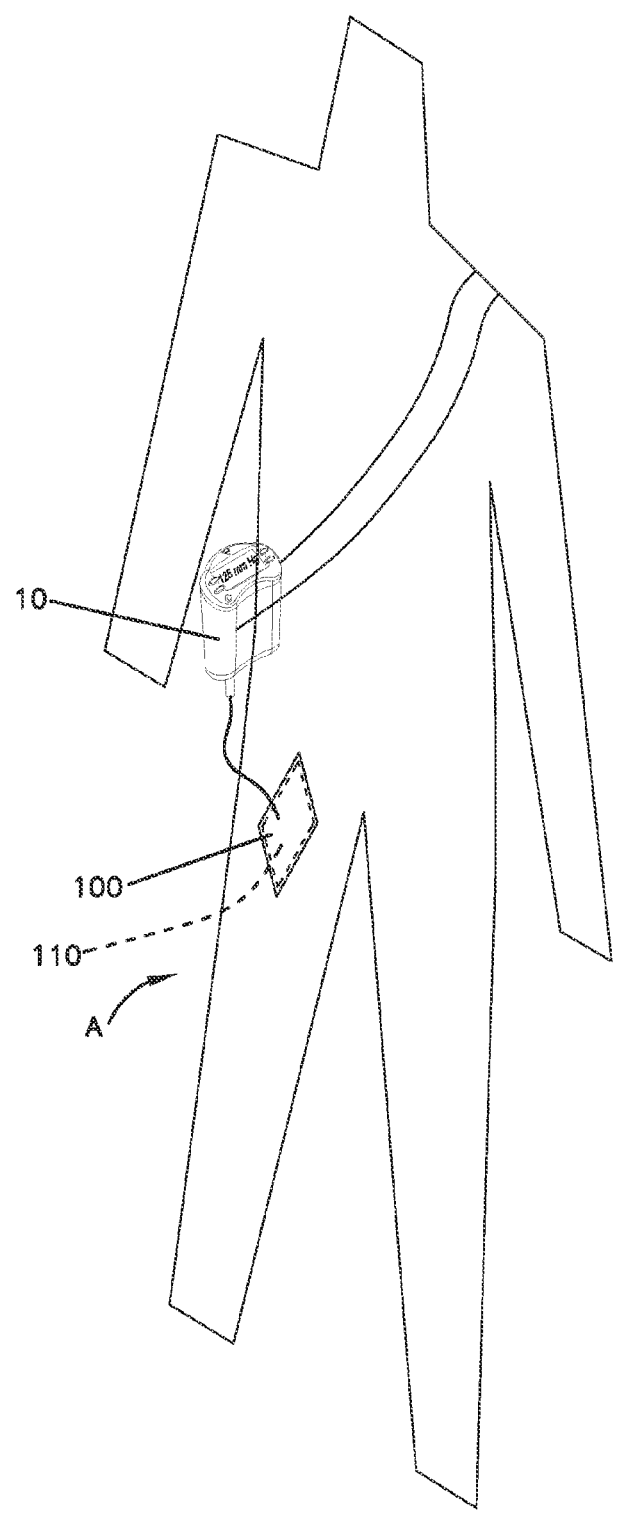
FIG. 8 is a schematic diagram illustrating a user having the device of FIGS. 4-6 affixed to his/her body.

In one embodiment, device 10 is shaped and sized such that the device 10 can be carried on the body of a user, for example, by a belt or other strap, such as around the torso of the user. FIGS. 8 and 9 illustrate two embodiments of a device according to the present disclosure being worn on the body of a user. FIG. 8 illustrates user A having device 10 held onto his/her torso by a shoulder strap. FIG. 9 illustrates user B having a device 10' (further described below) held onto his/her torso by a belt. For both users A, B, devices 10, 10' are operably connected to a wound 100, so as to provide negative pressure to wound 100 and remove exudate therefrom.

To facilitate carrying device 10 on the torso or other area of a user, housing 11 may be configured to better conform to the user. As can be seen in FIGS. 4 though 6, housing 11 can have a smooth outer surface with rounded corners and edges for providing comfort to the user. Additionally, as noted above, the front side 17 can have a concave surface 18 which allows device 10 to better wrap around and/or seat against the user. Housing 11 could be readily called streamlined.

Within this disclosure below are various features and element configurations that can be incorporated into or onto device 10 that may provide the desired features to device 10, e.g., lightweight, portability, etc. It should be understood that one or more of these features or elements may be present in or on device 10, in any combination, in order to provide a suitable negative pressure device.

1. Flexible Container or Bag

In certain embodiments, the device 10 of the present disclosure can include a flexible, expandable and/or deformable container, such as a bag or pouch similar to a catheter bag, to collect the exudate, rather than a rigid canister. Existing negative pressure wound healing devices (e.g., the KCI and Blue Sky Medical devices) utilize rigid canisters to collect the exudate from a wound. These canisters are large, round and bulky and limit the portability of the negative pressure wound healing devices. They also have problems with odors produced during the therapy.

For a flexible, expandable and/or deformable container, the volume of the bag, pouch or other container is designed to increase as the amount of exudate discharged into the bag increases. A flexible container has the advantages of being smaller, more flexible, less expensive, and better able to control odors.

In certain embodiments, the device 10 is configured to retain the flexible bag within its housing 11. In other embodiments, the device may include structures outside its housing for retaining the exudate. For example, in an alternate embodiment, illustrated in FIG. 7, the negative pressure device 10' is similar to device 10 of FIGS. 4-6, except that device 10' is configured to have a container, such as a flexible bag, present outside of housing 11. The device 10' includes a drain 25, which can be connected to an external container such as an expandable bag. FIG. 9 illustrates user B having device 10' affixed to himself/herself and connected to an expandable bag 50, which can be discretely positioned under clothing.

2. Semi-Rigid, Flexible, Expandable Canister

As a variation, device 10 can utilize a semi-rigid canister that is sufficiently flexible and expandable to change shape and size as exudate is collected. An example of such a container could have portions of the container that are rigid alternated with portions that are flexible, to provide a container that is expandable like a bellows. A ratchet mechanism could be included so that upon expansion of the container the vacuum force (applied to the wound) would not cause it to collapse. Pieces of compressed foam could be provided in the container which would expand when exposed to liquids from the exudate. Generally, the container size would be configured to expand as the amount of exudate deposited increases. In some embodiments, such a container would be desired because it would not require a system for moving a liquid from a vacuum space to a non-vacuum space.

3. Pump, Type 1

To move and remove the exudate from the wound to a collection bag, a pump of some type may generally be used. In some embodiments, device 10 of the present invention can include a dual action pump, such as including a 3-way check valve. In such an embodiment, one pump cylinder applies negative pressure to the wound dressing and the other pump cylinder discharges exudate into the catheter bag or other flexible container. The check valve would ensure that negative pressure is not applied to the catheter bag.

4. Pump, Type 2

In alternate embodiments, device 10 can include a peristaltic pump that uses rollers that squeeze and then open a tube, thus providing negative pressure on the input side and a positive pressure on the output side of the pump. The input side is connected to the wound dressing and provides suction, while the output side of the pump discharges exudate into the catheter bag. A peristaltic pump is particularly suitable due to its high reliability and low chance of cross contamination. In one embodiment, the pump may be a rotary peristaltic pump, in which, typically a fluid is conveyed within the confines of a flexible tube by waves of contraction placed externally on the tube which are produced mechanically, typically by rotating rollers which squeeze the flexible tubing against a support intermittently. Alternatively, the pump may be a linear peristaltic pump, in which, typically a fluid is conveyed within the confines of a flexible tube by waves of contraction placed externally on the tube which are produced mechanically, typically by a series of compression fingers or pads which squeeze the flexible tubing against a support sequentially. Peristaltic pumps may generally be advantageous as the electro-mechanical force mechanism (e.g. rollers driven by electric motor) does not make contact with the fluid, thus reducing the likelihood of inadvertent contamination.

5. Pump, Type 3

In another embodiment, device 10 can include a syringe pump. According to such an embodiment, a negative pressure would be created on the wound dressing when the syringe pump goes in one direction and then a positive pressure is created to expel exudate when the syringe pump goes in the other direction. This type of pump action could be used together with a 3-way check valve. The check valve would ensure that negative pressure is not applied to the catheter bag. With a syringe pump, typically a filled syringe is located on an electro-mechanical force mechanism (e.g. ram driven by electric motor) which acts on the plunger of the syringe to force delivery of the fluid contained therein. Alternatively, the syringe pump may comprise a double-acting syringe pump with two syringes such that they can draw saline from a reservoir, either simultaneously or intermittently. With a double acting syringe pump, the pumping mechanism is generally capable of both infusion and withdrawal. Typically, while fluid is being expelled from one syringe, the other syringe is receiving fluid therein from a separate reservoir. In this manner, the delivery of fluid remains continuous and uninterrupted as the syringes function in series. Alternatively, it should be understood that a multiple syringe pump with two syringes, or any number of syringes, may be used in accordance with the disclosure.

6. Pump, Type 4

In yet another embodiment, a bellows pump could be used. According to one embodiment, a motor arm with an oval shape would rotate over a bellows that would have negative pressure on the input and positive pressure on the output.

7. Multiple Vacuum Lines

In previous negative pressure systems, such as those discussed in the Background section of the disclosure, the systems normally use a single vacuum line that is operably connected to the wound and to the container collecting the exudate. According to one embodiment of this disclosure, a negative pressure device may be provided that has multiple vacuum lines (i.e., two or more).

The various lines could have different levels of suction force. These could be positioned in the wound in different locations, depending on, for example, the volume of wound at that location or the speed of healing desired at the location. For example, a deep part of the wound might have more suction applied to it than a shallow part of the wound. This might allow the wound to heal faster with less patient discomfort.

For larger wounds that occupy a large surface area, multiple lines may be preferred, with or without different levels of suction force, to better distribute the negative pressure.

8. Telemetry to Monitor Wound Status

Positioned with the foam or sponge, or connected to the vacuum line(s) could be a sensor system and/or wound monitoring system that might provide information to the user or the medical personnel about the healing progress of the wound. The sensors could be physically wired to device 10 or be wireless. Some of the parameters the system might measure include temperature, blood pressure, blood flow, $O_2$ level, pH, and pulse rate. These variables could help monitor wound healing rate and indicate whether infection set in. These variables could be measured to optimize the vacuum level and speed healing. Other types of sensors or indicators (e.g., infection indicators) can also be used. For example, according to one embodiment, a reagent that is configured to change color when infected exudate touches the reagent could be utilized in the vacuum line. When infected exudate passes through the vacuum line, the change of color of the vacuum line could provide a visual mechanism in detecting possible infection of the wound area.

9. Pressure Sensor

The negative pressure system could include a pressure sensor or other sensor or chip to help monitor the vacuum pressure. An increase of pressure at device 10 may indicate a blocked or clogged vacuum line. Additionally or alternatively, an increase of pressure at the wound may indicate completed healing or a problem with the healing process.

10. Semiconductor Chip or Other Identification

In some embodiments, it may be beneficial to include sensor(s) or semiconductor chip(s) in any portion of the system to insure proper equipment is used together.

11. Intelligent Vacuum Control Algorithm

In current negative pressure wound healing devices, such as those discussed in the Background section of the disclosure, patients can often feel discomfort at higher vacuum levels. In one embodiment according to the present disclosure, the vacuum system may include an intelligent vacuum control algorithm to better match a user's schedule and/or reduce pain. For example, the algorithm could be configured to gradually increase the vacuum levels, such as when a user is sleeping.

12. Spray Foam for Wound

The current procedure for most negative pressure wound dressings, using the systems discussed in the Background section of the disclosure, includes manually cutting a piece of foam or gauze to fit the size and shape of the wound. Because wounds are often of irregular shapes and/or volumes (e.g., depths), this manual procedure is time consuming and tedious.

According to one embodiment of the system of the present disclosure, an expandable foam (diagrammatically illustrated and referenced by numeral 110 in FIG. 8), such as that could be sprayed into the wound and would flow easily and then automatically conform to the wound shape, could be used. Such an in situ foam 110 could be designed to set automatically after exposure to air, light, or a curing source. Such an in situ forming foam 110 would save the medical personnel considerable time when changing wound dressings, while providing a much better fit of the foam 110 to the wound. The spray 110 would preferably be biocompatible and biodegradable, and could contain active ingredients such as medications to reduce infections or speed healing.

13. Dressing Cover with Multiple Holes to Introduce Vacuum

Generally, the foam material is covered with a dressing material to protect the wound and the foam. In conventional systems, such as those discussed in the Background section of the disclosure, the dressing includes a single hole therethrough, for application of the vacuum. According to one embodiment of the present disclosure, a wound cover or drape having multiple holes in the surface facing the wound could be provided. The vacuum tube would be sandwiched between this layer and a top layer, such as a clear plastic layer. Spacers, such as foam, may be provided between the layers to better provide a volume for the end of the vacuum tube. Having multiple holes through the layer against the wound diffuses the vacuum as it is applied to the wound, such as to the foam or gauze in the wound. This would make the dressing more effective and comfortable for the patient.

Referring now to FIG. 8, as discussed previously, a user A is shown having device 10 held onto his/her torso by a shoulder strap and operably connected to wound 100. FIG. 9 illustrates a user B having device 10' held onto his/her torso by a belt and operably connected to wound 100. Devices 10, 10' provide negative pressure to wound 100, removing exudate therefrom and speeding healing.

The above specification and examples are believed to provide a complete description of the manufacture and use of particular embodiments of the disclosure. It is understood that various other configurations of containers and dividing elements are suitable. For example, container bodies other than four sided ones may be used; for example, round, pentagonal, hexagonal, etc. bodies may be used. Divider elements that divide the interior volume of the container body into three or four or more may also be used. It is understood by those skilled in the art that containers may be made by generally any suitable process, not just those described herein. Various other methods of making containers according to the present disclosure are suitable.

Because many embodiments of the disclosure can be made without departing from the spirit and scope of the inventive aspects, the true scope and spirit of the inventive aspects reside in the broad meaning of the claims hereinafter appended.

What is claimed is:

1. A system for applying negative pressure on a wound, the system comprising:
    a device including structure configured to provide negative pressure on the wound;
    a dressing material sealably covering the wound and an expandable spray-in foam located within the wound below the dressing material, the spray-in foam exposed to the negative pressure provided by the device, wherein the spray-in foam has an initial flowable state and a final set state wherein the spray-in foam automatically substantially conforms to a shape of the wound; and
    a plurality of vacuum lines extending between the device and the dressing material, wherein each of the plurality of vacuum lines is used to provide negative pressure to the wound sealably covered by the dressing material.

2. A system according to claim 1, wherein the device is configured to be mounted on a person.

3. A system according to claim 1, wherein the device weighs no more than about 3 lbs.

4. A system according to claim 3, wherein the device weighs no more than about 2.5 lbs.

5. A system according to claim 4, wherein the device weighs no more than about 2 lbs.

6. A system according to claim 5, wherein the device weighs no more than about 1.5 lbs.

7. A system according to claim 1, wherein the housing of the device has a volume of no more than about 125 in$^3$.

8. A system according to claim 1, wherein the device includes a housing having at least a flexible and expandable portion.

9. A system according to claim 1, wherein the structure within the device configured to provide negative pressure on the wound includes a peristaltic pump.

10. A system according to claim 1, wherein the structure within the device configured to provide negative pressure on the wound includes a syringe pump.

11. A system according to claim 1, wherein the pump includes a three-way check valve to prevent application of negative pressure to the device.

12. A system according to claim 1, further comprising a container connected to the device for storing extrudate obtained by the applied pressure on the wound.

13. A system according to claim 12, wherein the container is located outside of a housing of the device, the housing configured to enclose the structure for providing negative pressure on the wound.

* * * * *